(12) United States Patent
Kim

(10) Patent No.: US 12,391,704 B2
(45) Date of Patent: Aug. 19, 2025

(54) METHOD FOR SYNTHESIZING DECURSIN DERIVATIVE

(71) Applicant: PRG S&TECH INC., Busan (KR)

(72) Inventor: Min Ju Kim, Busan (KR)

(73) Assignee: PRG S&TECH INC., Busan (KR)

( * ) Notice: Subject to any disclaimer, the term of this patent is extended or adjusted under 35 U.S.C. 154(b) by 654 days.

(21) Appl. No.: 17/787,937

(22) PCT Filed: Nov. 6, 2020

(86) PCT No.: PCT/KR2020/015492
§ 371 (c)(1),
(2) Date: Jun. 22, 2022

(87) PCT Pub. No.: WO2021/132872
PCT Pub. Date: Jul. 1, 2021

(65) Prior Publication Data
US 2023/0063754 A1 Mar. 2, 2023

(30) Foreign Application Priority Data
Dec. 24, 2019 (KR) .................. 10-2019-0174080

(51) Int. Cl.
*C07D 493/04* (2006.01)
(52) U.S. Cl.
CPC ........ *C07D 493/04* (2013.01); *C07B 2200/13* (2013.01)
(58) Field of Classification Search
CPC ... C07D 493/04; C07B 2200/13; A61P 43/00; A61K 31/366

USPC ....................................................... 549/282
See application file for complete search history.

(56) References Cited

U.S. PATENT DOCUMENTS

2020/0048274 A1  2/2020 Park et al.

FOREIGN PATENT DOCUMENTS

| JP | 2016-522821 A | 8/2016 |
|---|---|---|
| KR | 10-2009-0037185 A | 4/2009 |
| KR | 10-2010-0008808 A | 1/2010 |
| KR | 10-2018-0019490 A | 2/2018 |
| KR | 10-2018-0119490 A | 11/2018 |
| WO | 2018-199633 A1 | 11/2018 |

OTHER PUBLICATIONS

Aldrich, Aldrich Catalogue, 1998-1999, pp. 1154 and 1570). (Year: 1999).*

(Continued)

*Primary Examiner* — Taylor V Oh
(74) *Attorney, Agent, or Firm* — Revolution IP, PLLC

(57) ABSTRACT

The present invention relates to a novel method for synthesizing a decursin derivative, the method comprising: a step (I) for preparing a solution by mixing cinnamyl bromide and an N-Methyl-2-pyrrolidone [N-Methyl-2-pyrrolidone (NMP)] solvent; a step (II) for preparing a solution by mixing decursinol, a tetrahydrofuran (THF) solvent, and sodium hydride (NaH); and a step (III) for obtaining a decursin derivative by mixing the solutions prepared in step (I) and step (II). The method can increase the yield of the obtained decursin derivative compound and enables mass production.

5 Claims, 1 Drawing Sheet

(56) References Cited

OTHER PUBLICATIONS

Japan Chemical Society, Experimental Chemistry Guide Book, Marzen Co., Ltd., pp. 130 to 131.
Office Action of Japanese Patent Application No. 2022-539009 mailed Jun. 9, 2023.
International Search Report for PCT/KR2020/015492 mailed Feb. 23, 2021 from Korean Intellectual Property Office.
Lee, K. et al., "Synthesis of (S)-(ϕ)-decursin and its analogues as potent inhibitors of melanin formation in B16 murine melanoma cells", European Journal of Medicinal Chemistry, vol. 45, Issue 12, Dec. 2010, pp. 5567-5575.
Lee, W. et al., "Suppressive activities of KC1-3 on HMGB1-mediated septic responses", Biochemical Pharmacology, vol. 163, May 2019, pp. 260-268.

* cited by examiner

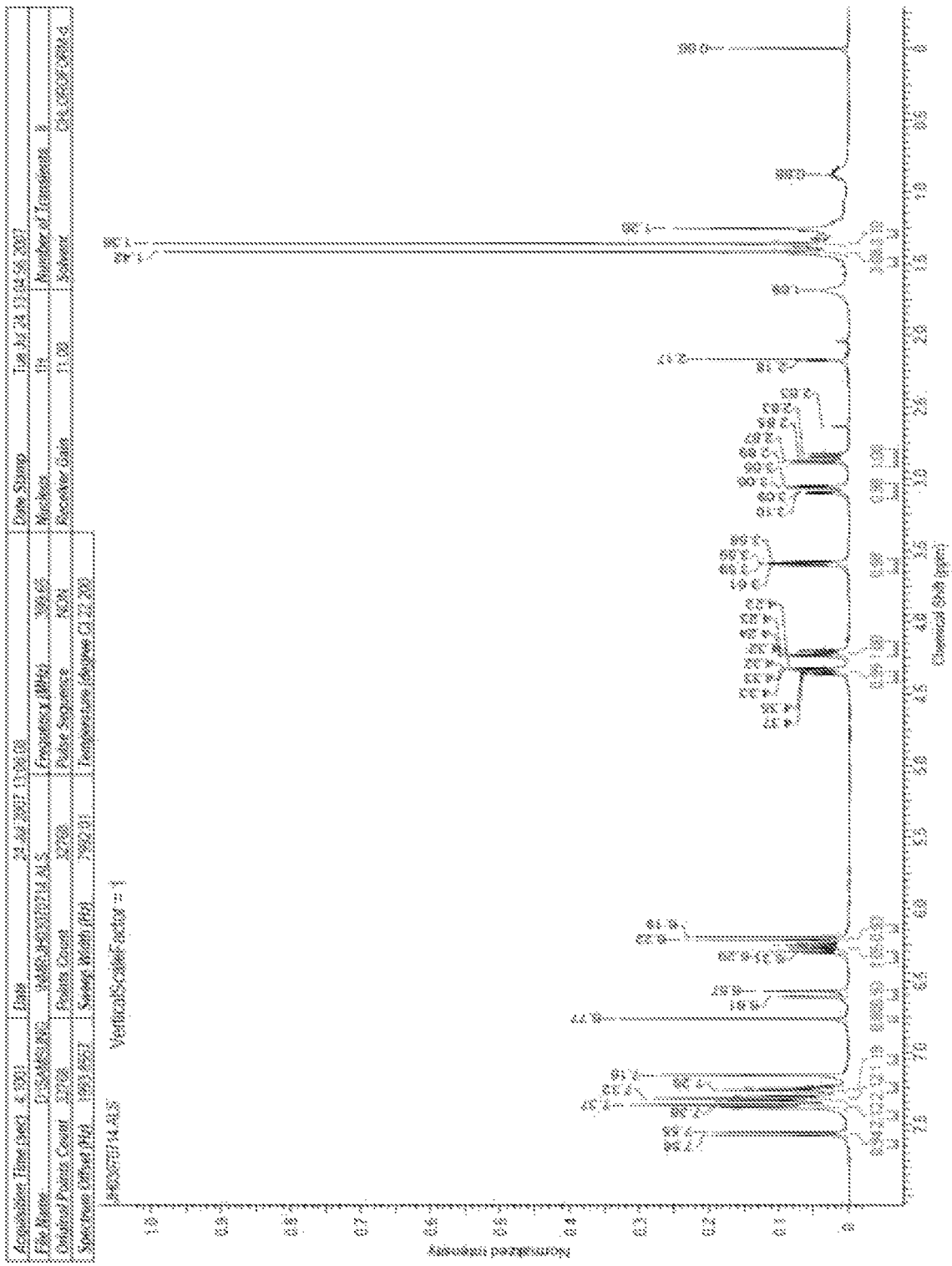

METHOD FOR SYNTHESIZING DECURSIN DERIVATIVE

CROSS REFERENCE TO PRIOR APPLICATIONS

This application is a National Stage Application of PCT International Patent Application No. PCT/KR2020/015492 filed on Nov. 6, 2020, under 35 U.S.C. § 371, which claims priority to Korean Patent Application No. 10-2019-0174080 filed on Dec. 24, 2019 which are all hereby incorporated by reference in their entirety.

TECHNICAL FIELD

The present disclosure relates to a novel method for synthesizing a decursin derivative.

BACKGROUND ART

As human life expectancy increases, interest in the process of aging has been actively grown. However, there are still few areas that are clearly known, and recent studies are focused on genetic or molecular mechanisms of aging, mainly targeting human progeria.

Progeria or Hutchinson Gilford progeria syndrome (HGPS) is a fatal, rare genetic disorder that causes premature aging in young children. Children with progeria appear normal in early infancy but begin to show significant growth retardation around 9-24 months, eventually leading to short stature and low weight. In addition, with distinguishing facial shapes, systemic atherosclerosis, cardiovascular diseases, stroke, and hip joint dislocation are accompanied, and loss of subcutaneous fat layer, defective nail, joint hardening, and skeletal damage also appear. These pediatric patients with progeria usually die between the ages of 8-21 due to heart diseases, and average life expectancy is about 13 years.

HGPS is a very rare autosomal dominant genetic disease caused by a silent mutation of G608G in lamin A (LMN A). The mutation causes creation of a new cleavage donor site and production of progerin (Prg) which is a product of a selective cleavage site from which 50 amino acids in the C-terminal domain of lamin A are deleted.

Expression of progerin induces morphological changes such as irregularity in nuclear membranes or a decrease in nuclear-cytoplasmic lamin A, and suppression of progerin expression also induces a decrease in nuclear transformation. Thus, progerin is determined as a major factor of HGPS.

Accordingly, in Korean Patent Laid-Open Publication No. 10-2018-0019490, a decursin derivative compound, a novel compound, has been proven to be effective in treating aging-related diseases and preventing or ameliorating wrinkles. However, due to a low yield of the decursin derivative compound, there has been a limitation in mass production.

Therefore, required is research on a novel synthesis method capable of increasing the yield of the decursin derivative compound and enabling mass production.

DISCLOSURE

Technical Goals

An object of the present disclosure is to provide a method for synthesizing a novel decursin derivative, capable of increasing the yield of a decursin derivative compound and enabling mass production.

Technical Solutions

To achieve the above object, example embodiments of the present disclosure provide a method for synthesizing a decursin derivative, the method including (I) preparing a solution by mixing cinnamyl bromide and an N-methyl-2-pyrrolidone (NMP) solvent; (II) preparing a solution by mixing decursinol, a tetrahydrofuran (THF) solvent, and sodium hydride (NaH); and (III) obtaining a decursin derivative represented by Chemical Formula 1 by mixing the solutions prepared in (I) and (II).

[Chemical Formula 1]

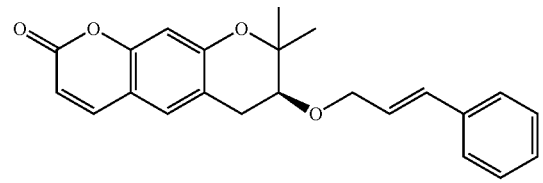

Advantageous Effects

According to a novel method for synthesizing a decursin derivative compound according to example embodiments of the present disclosure, it is possible to increase the yield of the obtained decursin derivative compound, ensure a yield of 80% or more after an additional recrystallization process, and enable mass production as well.

BRIEF DESCRIPTIONS OF THE DRAWINGS

FIG. 1 is a diagram showing NMR results of a decursin derivative synthesized according to an example embodiment of the present disclosure.

MODES FOR CARRYING OUT INVENTION

Hereinafter, the present disclosure will be described in detail.

The present inventors were able to increase the yield of obtained decursin derivative compounds when the synthesis was performed using an N-methyl-2-pyrrolidone (NMP) solvent, a tetrahydrofuran (THF) solvent, and sodium hydride (NaH) in the process of synthesizing a decursin derivative from cinnamyl bromide and decursinol, and completed the present disclosure by identifying an optimal novel synthesis method deriving a high yield of 80% or more after an additional recrystallization process.

An example embodiment of the present disclosure provides a method for synthesizing a decursin derivative, including (I) preparing a solution by mixing cinnamyl bromide and an N-methyl-2-pyrrolidone (NMP) solvent; (II) preparing a solution by mixing decursinol, a tetrahydrofuran (THF) solvent, and sodium hydride (NaH); and (III) obtaining a decursin derivative represented by Chemical Formula 1 by mixing the solutions prepared in (I) and (II).

[Chemical Formula 1]

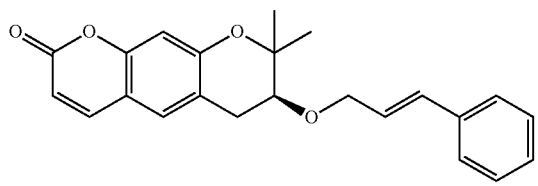

Here, the cinnamyl bromide and NMP are included in a weight ratio of 1:(5 to 10), and a solution may be prepared by mixing cinnamyl bromide and NMP and then stirring the mixture at 15-25° C.

In addition, the decursinol, THF, and NaH are included in a weight ratio of (5 to 10):(50 to 100):1, and after preparing a solution by mixing the decursinol and THF and stirring the same at 15-25° C., addition of NaH is followed at −5-5° C. for preparation.

In addition, the obtaining of the decursin derivative may include adjusting pH of the mixed solution prepared in (III) to 7 or less (first step); obtaining an organic layer from the solution of the first step (second step); concentrating the organic layer obtained in the second step under reduced pressure to obtain a reaction solution (third step); and obtaining the decursin derivative by heat-treating and cooling the reaction solution obtained in the third step, followed by filtration and drying (fourth step).

Through the method for synthesizing the decursin derivative as described above, it was possible to obtain a (7S)-(+)-8,8-dimethyl-7-(3-phenyl-allyloxy)-7,8-dihydro-6H-pyrano [3,2-g]chromen-2-one (SLC-D011) compound with a yield of 58%, which is an optimal synthesis method to acquire a higher yield than the conventional synthesis method with a yield of 30-40%.

In this case, the method may further include recrystallizing the obtained decursin derivative.

The recrystallizing may include preparing a reaction solution by mixing acetone with the obtained decursin derivative (first step); preparing a reaction solution by mixing a seed with the reaction solution of the first step (second step); mixing the reaction solution of the second step with isopropyl alcohol and concentrating the mixture under reduced pressure (third step); and obtaining a decursin derivative by filtering and drying the solution concentrated under reduced pressure in the third step (fourth step).

Here, the seed is a decursin derivative product having a purity of 99.5% or more and 0.10% or less of individual related substances, facilitating crystallization when the seed is used in the crystallization process. In addition, it is possible to remove the related substances while control of polymorph is easy.

By further including the recrystallizing of the decursin derivative, it was determined that the (7S)-(+)-8,8-dimethyl-7-(3-phenyl-allyloxy)-7,8-dihydro-6H-pyrano [3,2-g]chromen-2-one (SLC-D011) compound was obtainable with a very high yield of 86%.

If the range of reactant content, temperature, and mixing conditions are out of the range in the method for synthesizing a decursin derivative, the yield of the decursin derivative compound according to an example embodiment of the present disclosure becomes significantly lowered or mass production is hardly possible, which may be cost ineffective.

In addition, the (7S)-(+)-8,8-dimethyl-7-(3-phenyl-allyloxy)-7,8-dihydro-6H-pyrano [3,2-g]chromen-2-one (SLC-D011) compound which is a decursin derivative synthesized according to an example embodiment of the present disclosure may effectively be used in the treatment of aging-related diseases such as Hutchinson Gilford progeria syndrome (HGPS) and Werner syndrome, used as a cosmetic composition for preventing or ameliorating wrinkles since the compound is able to increase collagen production in skin cells, and also applied to a pharmaceutical composition and health functional food for the prevention and treatment of atopic dermatitis.

Hereinafter, the present disclosure will be described in more detail through example embodiments. The example embodiments are merely for describing the present disclosure in more detail, and it will be apparent to those of ordinary skill in the art to which the present disclosure pertains that the scope of the present disclosure is not limited by the example embodiments according to the gist of the present disclosure.

<Comparative Example 1> Synthesis of (+)-decursin Derivative (SLC-D011) in an Ether-Form

[Scheme 1]

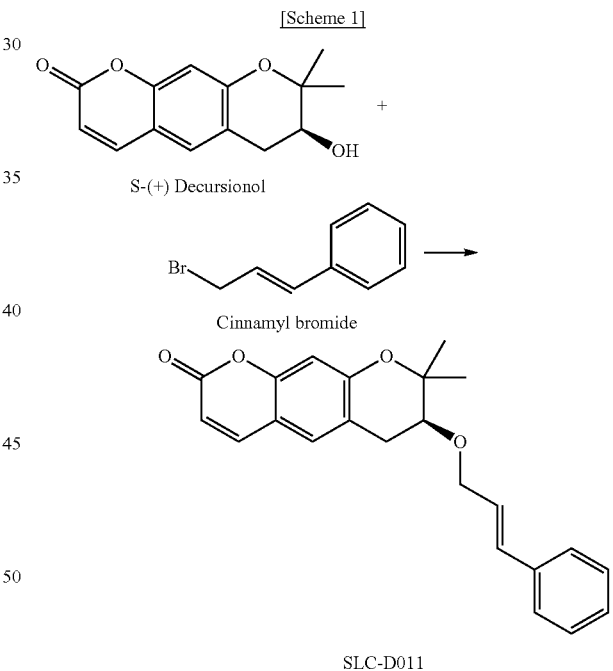

As in Scheme 1, (S)-(+)-decursinol (SLC-B001, 2.33 g, 9.47 mmol, 1 eq) was dissolved with N,N-dimethylformamide (DMF, 10 ml) in a 100 ml round flask in the presence of $N_2$ gas, and the flask was then installed in a low-temperature reactor set at −20° C.

After (E)-cinnamyl bromide ((3-bromo-propenyl)-benzenel, 2.8 g, 14.2 mmol, 1.5 eq) and sodium hydride (NaH, 60%, 757 mg, 18.9 mmol, 2 eq) were added to the reaction mixture solution and stirred for 4 hours, and 3 ml of distilled water was added. After 10 minutes, the mixture was taken out of the low-temperature reactor to be separated twice with 200 ml of dichloromethane and 200 ml of distilled water.

The organic layer was collected, dehydrated with sodium sulfate, and filtered. The filtrate was then concentrated under reduced pressure.

The concentrate was subjected to silica gel column separation (ethyl acetate:n-hexane=gradient elution to 1:3 from 1:10) to obtain 1.21 g (35.3%) of (7S)-(+)-8,8-dimethyl-7-(3-phenyl-allyloxy)-7,8-dihydro-6H-pyrano [3,2-g]chromen-2-one (SLC-D011); yield of 35.3%, white solid, mp: 143° C., $R_f$=0.39 (2:1 n-hexane-ethyl acetate); $[\alpha]^{25}_D$+ 117.6 (c=1, CHCl$_3$); $^1$H NMR (400 MHz, CDCl$_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=60, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s CH$_3$-8), 1.36 (3H, s, CH$_3$-8); $^{13}$C NMR (100 MHz, acetone-d$_6$) $\delta_C$ 161.2 (C-2), 157.8 (C-9a), 155.3 (C-10a), 144.5 (C-4), 137.9 (C-4'), 132.9 (C-3'), 130.4 (C-5), 129.6 (C-6', C-8'), 128.6 (C-7'), 127.5 (C-2'), 127.4 (C-5', C-9'), 118.3 (C-5a), 113.7 (C-3), 113.6 (C-4a), 104.5 (C-10), 78.8 (C-7), 76.4 (C-8), 70.8 (C-1'), 27.8 (C-6), 26.1 (CH$_3$-8), 22.2 (CH$_3$-8); ESI-MS: m/z=363 [M+H]$^+$. Anal Calc for C$_{23}$H$_{22}$O$_4$: C, 76.22; H, 6.12. Found: C, 76.20; H, 6.10.

<Comparative Example 2> Synthesis of (+)-decursin Derivative (SLC-D011) in an Ether-Form Synthesis was performed under the same conditions as in <Comparative Example 1>, except that potassium hydroxide was used instead of sodium hydride (NaH) in <Comparative Example 1>.

As a result, it was determined that (75)-(+)-8,8-dimethyl-7-(3-phenyl-allyloxy)-7,8-dihydro-6H-pyrano [3,2-g]chromen-2-one (SLC-D011) which is a white solid decursin derivative was obtained in a yield of 44%.

$^1$H NMR (400 MHz, CDCl$_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=60, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s CH$_3$-8), 1.36 (3H, s, CH$_3$-8).

<Example 1> Synthesis of (+)-decursin Derivative (SLC-D011) in a Novel Ether-Form 1.1 Preparation of (E)-Cinnamyl Bromide Solution (Solution 1)

(E)-Cinnamyl bromide (12.4 kg, 60.9 moles, 1.24 eq) and N-methyl-2-pyrrolidone (NMP, 63.8 kg) were mixed in a reactor and stirred at 15-25° C.

1.2 Preparation of an S-Decursinol Solution (Solution 2)

S-Decursinol (12.1 kg, 49.1 moles, 1.0 eq) and tetrahydrofuran (THF, 122 kg) were mixed in a reactor and stirred at 15-25° C. Sodium hydride (NaH, 1.81 kg, 75.4 moles, 1.54 eq) was slowly added for at least 1 hour while maintaining the temperature in the reactor at −5-5° C.

1.3 Mixing the Solution 1 and the Solution 2

The Solution 1 was added to the Solution 2 while maintaining the internal temperature at −5-5° C., followed by stirring for at least 10 hours.

After completion of the reaction, acetic acid (6.6 kg) was added, the pH of the reaction solution was checked to be 7 or less (<7), and the mixture was stirred at −5-5° C. for to 1-3 hours. Methyl tertiary butyl ether (MTBE, 92 kg) and purified water (124 kg) were added, and the mixture was stirred at 20-30° C. for 20-30 minutes. When the layers were separated, the organic layer was left in the reactor, and the aqueous layer was discarded. Purified water (62 kg) was added to the organic layer, and the layers were separated after stirring for 20 minutes. Then, the aqueous layer was discarded, and purified water (62 kg) was added to the organic layer again. After stirring for 20 minutes to separate the layers, the aqueous layer was discarded.

The organic layer was added with toluene (62 kg) at 40° C. or less and then concentrated under reduced pressure until the volume becomes 25-37 L. Then, toluene (62 kg) was re-added, and concentration was repeated under reduced pressure until the solution becomes 25-37 L.

Thereafter, the reaction solution was heated at 80-85° C. for 2 hours, stirred at 45-50° C. for 2-4 hours, and then cooled after stirring at −5-5° C. for 4-8 hours.

The product was filtered using a centrifuge filter, and the filtered product was washed with cooled toluene (−5-5° C., 27 kg), followed by drying at 35-40° C. until the residual toluene becomes 0.5% or less.

It was determined that the dried product was a white solid of (7S)-(+)-8,8-dimethyl-7-(3-phenyl-allyloxy)-7,8-dihydro-6H-pyrano [3,2-g]chromen-2-one (SLC-D011) with yield of 10.4 kg (58%), 99.0% purity (HPLC Area %), and 98.6% content.

$^1$H NMR (400 MHz, CDCl$_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=60, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s CH$_3$-8), 1.36 (3H, s, CH$_3$-8)(FIG. 1).

<Example 2> Recrystallization of SLC-D011

(7S)-(+)-8,8-dimethyl-7-(3-phenyl-allyloxy)-7,8-dihydro-6H-pyrano [3,2-g]chromen-2-one (SLC-D011, 10.4 kg, 26.7 moles) obtained in <Example 1> was added to the reactor. Acetone (68 kg) was added, and stirring was performed at 50-55° C. for 10-40 minutes. While maintaining the solution temperature to 50-55° C., the reaction solution was filtered through a cartridge filter. Then, the filtrate was stirred at 50-55° C. for 40 minutes.

After cooling the reaction solution to 40-45° C. slowly over 0.5 to 1 hour, 100 g of seed (product with 99.5% or more of purity, 0.10% or less of individual related substances) was added, and stirring was performed for 1.5-2.5 hours. Thereafter, the reaction solution was cooled to 20-25° C. for 0.5-1 hour.

While maintaining the temperature at 20-25° C., isopropyl alcohol (127 kg) was added for 4-8 hours. The reaction solution was distilled under reduced pressure at 25° C. or less until the solution volume becomes 190-210 L. Then, the reaction solution was cooled to 0-5° C. for 2-3 hours and stirred for 12-16 hours to obtain a product.

The product was filtered using a filter dryer, and the filtered product was washed twice with isopropyl alcohol (15 kg×2). The product was placed in a dryer to be dried at 20-30° C. for 20-24 hours. It was determined that repurified (7S)-(+)-8,8-dimethyl-7-(3-phenyl-allyloxy)-7,8-dihydro-6H-pyrano [3,2-g]chromen-2-one (SLC-D011) was a white solid with the following features: yield: 9.05 kg (86%), purity (HPLC): 99.9%, chiral purity: 100%, content (HPLC): 98.3%, LOD (Loss on Drying): 0.1%, Water content (Karl Fisher): 0.1%, DSC: Onset 149° C. Peak 150.3° C., Melting point: 148-149° C.

$^1$H NMR (400 MHz, CDCl$_3$): $\delta_H$ 7.56 (1H, d, J=9.6 Hz, H-4), 7.38-7.23 (5H, m, H-5', H-6', H-7', H-8', H-9'), 7.15 (1H, s, H-5), 6.76 (1H, s, H-10), 6.59 (1H, d, J=16.0 Hz, H-3'), 6.30-6.23 (1H, m, H-2'), 6.20 (1H, d, J=9.6 Hz, H-3), 4.34 (1H, dd, J=6.0, 12.8 Hz, H-1a'), 4.21 (1H, dd, J=60, 12.4 Hz, H-1b'), 3.59 (1H, dd, J=5.2, 7.6 Hz, H-7), 3.07 (1H, dd, J=4.8, 16.0 Hz, H-6a), 2.85 (1H, dd, J=7.2, 16.4 Hz, H-6b), 1.41 (3H, s CH$_3$-8), 1.36 (3H, s, CH$_3$-8).

What is claimed is:

1. A method for synthesizing a decursin compound, comprising:

(I) preparing a solution by mixing cinnamyl bromide and an N-methyl-2-pyrrolidone (NMP) solvent;

(II) preparing a solution by mixing decursinol, a tetrahydrofuran (THF) solvent, and sodium hydride (NaH);

(III) obtaining a decursin compound represented by Chemical Formula 1 by mixing the solutions prepared in (I) and (II),

[Chemical Formula 1]

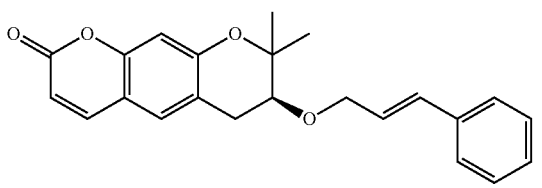

(IV) recrystallizing the obtained decursin compound.

2. The method of claim 1, wherein the cinnamyl bromide and NMP are included in a weight ratio of 1:(5 to 10).

3. The method of claim 1, wherein the decursinol, THF, and NaH are included in a weight ratio of (5 to 10):(50 to 100):1.

4. The method of claim 1, wherein the obtaining of the decursin compound comprises:

adjusting pH of the mixed solution prepared in (III) to 7 or less (first step);

obtaining an organic layer from the solution of the first step (second step);

concentrating the organic layer obtained in the second step under reduced pressure to obtain a reaction solution (third step); and obtaining the decursin compound by heat-treating and cooling the reaction solution obtained in the third step, followed by filtration and drying (fourth step).

5. The method of claim 1, wherein the recrystallizing comprises:

preparing a reaction solution by mixing acetone with the obtained decursin compound (first step);

preparing a reaction solution by mixing a seed with the reaction solution of the first step (second step);

mixing the reaction solution of the second step with isopropyl alcohol and concentrating the mixture under reduced pressure (third step); and obtaining a decursin compound by filtering and drying the solution concentrated under reduced pressure in the third step (fourth step).

* * * * *